United States Patent
Ross

(10) Patent No.: US 10,947,496 B2
(45) Date of Patent: *Mar. 16, 2021

(54) MOLDING SYSTEM FOR FUNGAL STRUCTURES

(71) Applicant: Mycoworks, Inc., San Francisco, CA (US)

(72) Inventor: Philip Ross, San Francisco, CA (US)

(73) Assignee: MycoWorks, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/884,740

(22) Filed: Jan. 31, 2018

(65) Prior Publication Data

US 2018/0148682 A1 May 31, 2018

Related U.S. Application Data

(63) Continuation of application No. 15/230,438, filed on Aug. 7, 2016, now Pat. No. 9,951,307, which is a continuation of application No. 13/305,576, filed on Nov. 28, 2011, now Pat. No. 9,410,116.

(60) Provisional application No. 61/417,408, filed on Nov. 27, 2010.

(51) Int. Cl.
  *C12N 1/22* (2006.01)
  *A01G 18/00* (2018.01)
  *C12N 1/14* (2006.01)

(52) U.S. Cl.
  CPC ............... *C12N 1/22* (2013.01); *A01G 18/00* (2018.02); *C12N 1/14* (2013.01)

(58) Field of Classification Search
  CPC ........................................................ C12N 1/14
  See application file for complete search history.

(56) References Cited

U.S. PATENT DOCUMENTS

2008/0145577 A1* 6/2008 Bayer .................... C05D 9/00
                                                428/35.6

OTHER PUBLICATIONS

Tweddell et al. New Zealand J of Crop and Horticultural Science, 1993, 21:283-289.*
Kurtzman Micrologia Aplicada International, 2010, 22(2():63-78.*
Panikov et al., FEMS Microbiol Ecol., 2007, 59:500-512.*

* cited by examiner

*Primary Examiner* — Bin Shen
(74) *Attorney, Agent, or Firm* — Temmerman Law; Mathew J. Temmerman

(57) ABSTRACT

A molding system for forming an inoculated lignocellulose based medium into a fungal molded shape, the molding system comprising a vessel within which environmental conditions are regulated, the vessel comprising an inoculated lignocellulose based medium capable of supporting growth of saprophytic fungi without any secondary organisms displacing the process through infection a secondary organic material layered near the top and bottom of the inoculated lignocellulose based medium, a hard mold containing the flexible vessel; and a compressive system for applying a primary compressive pressure of at least 10 PSI to the lignocellulose based medium such that it takes on a fungal molded shape.

19 Claims, 10 Drawing Sheets

MOLDING SYSTEM FOR FUNGAL STRUCTURES

RELATED APPLICATIONS

This application is a continuation application of U.S. patent application Ser. No. 15/230,438 filed Aug. 7, 2016 and patented as U.S. Pat. No. 9,951,307 on Apr. 24, 2018, and which is a continuation application of U.S. patent application Ser. No. 13/305,576 filed Nov. 28, 2011 and granted Aug. 9, 2016 as U.S. Pat. No. 9,410,116, and which claims priority from U.S. provisional application Ser. No. 61/417,408, which was filed on Nov. 27, 2010. The disclosures of these applications are incorporated herein as if set out in full.

BACKGROUND OF THE DISCLOSURE

Technical Field of the Disclosure

The present embodiment relates in general to methods for creating organically derived building materials using the growth of fungal tissue. More specifically, the present embodiment relates to a method for growing engineered building materials in the form of a moldable substrate which can be used for a wide range of manufacturing and construction applications.

Description of the Related Art

Fungi are a kingdom of organisms which are numerous and diverse, and are distinguished in part by the habits and forms of representative members' vegetative growth and reproduction. While fungi are incredibly diverse in form, habit, and environmental requirements, fungi are easily identifiable by the shared common trait of consuming living or once living organic matter. Like animals, fungi feed on the bodies of other organisms as their primary source of constituent matter and energy, and are the primary decomposers and recyclers of materials on the planet. Fungi are distributed through the depths of the ocean, within and amongst the bodies of all the higher organisms, and have spores that travel to the heights of the atmosphere and out into space. The spores of fungi are resilient enough to enter the vacuum of space and return to earth, growing once again when situated in welcoming terrestrial conditions.

One of the primary forms of material that fungi assist in decomposing are the plants, trees and other organisms that weave airborne carbon into a terrestrial form with energy derived from sunlight. Chlorophyl based organisms transform sunglight into the sugars, carbohydrates and other macromolecules that constitute a plant's various cells, tissues and organs. Many of these sugars in plants are tightly bound within the form of lignin and cellulose, which are composed from an intricately linked glucose based polymer, the constituent element of which comprises the dense structural elements of the plant's body. Many different kinds of fungi have evolved the ability to break down both lignin and cellulose, and transform it into chitin, the resiliently hard molecule that fungi use to build their cell walls. Fungi are both strong and flexible, and are capable of synthesizing (and also metabolizing) a wide range of enzymes, oxidative compounds, alcohols and other caustic chemical agents that can break the strong hydrogen bonds that contribute to the rigidity and structure of cellulose. Many fungi that feed upon cellulose infect and colonize their preferred nutrient source by means of hyphal cells that grow in a vegetative manner from the apical ends of the cell. These hypha are characterized by apical growth patterns that include bifurcations, ramifications and other branching cellular nodes that are capable of secreting and reabsorbing the above mentioned caustic agents, and are capable of breaking down and digesting the hardest known woods. These growing nodes increase the area and potential connectivity of the collective hyphal structures, allowing the fungal cells to infiltrate, connect and modify a wide range of endogenous environments that it might be situated within. The Polypores are a group of fungi that are known for their durability, strength and long life span. The polypores are wide in their geographic distribution and can breakdown and utilize a wide range of plant life that is rich in sources of lignin and cellulose.

In recent years fungi have come to be an accepted material for a range of consumer and building applications, and are increasingly being used in the place of plastics, urethanes and other fossil fuel dependent compounds. In addition to its strength and durability, dried fungus has many other beneficial qualities: it is nontoxic, fire-resistant, mold resistant, water-resistant and a great thermal insulator amongst other salient features. Fungi can be processed with less energy and materials than conventional manufacturing, and can be grown in a way that contributes to good stewardship of renewable resources. Different methods have been developed to utilize the fungi's capabilities for rapidly digesting and transforming a range of biological materials, yet all are due in great part to the physical characteristics of the growing hyphal cells of the fungi, which form a complexly interwoven tissue that is called mycelium.

This mycelial web can be as strong and resilient as wood, and acts as a bonding agent for a wide range of materials that it might be incorporated within. The mycelium itself is remarkably sensitive to local environmental conditions, and the current state of the art is advancing with new means for adjusting and modifying this environment in ways to cause the fungus to grow in a desired manner and with desired characteristics. The state of the art in this field is new and primarily consists of simple molds and laminated substrates, and there is a need for innovative techniques in both the forming, conditioning and manufacturing of the growing fungi and the material that it generates.

Recent advancements in the art include a fungus that is grown for the purposes of providing a polystyrene replacement that is based upon organically derived materials and feedstock. This method involves placing fungus and agricultural or industrial waste products such as rice husks, wheat husks or sawdust into a mold in the form of a panel wherein incubation occurs for several days. During the incubation period the inoculated fungal substrate forms a mycelial network that binds the materials together, slowly solidifying into the shape of the form it was cast within. After incubation, the entire mixture may be dried so that further fungal growth is retarded. The finished panel product exhibits the characteristics of the original materials it was grown from (such as the strength or thermally insulating qualities of the fibers), which are now "glued" together by the fungus. Though a good insulator, this panel must be formed in combination with a laminated back or sandwich of a thin, rigid material when greater tensile strength is desired. The final products made through this process are lightweight, and when its consumer cycle is complete it can be added to landfill or compost due to the sole use of natural ingredients. The product has also been used as a replacement for Styrofoam packaging, both with and without rigid backings, and will soon be available as home and building insulation. This method does not however provide a means for producing environmentally friendly building materials that are also strong and durable enough for the tolerances and demands of many other manufacturing and construction applications than a fragile Styrofoam type formulation.

Another existing system uses mycelium to create materials composed of a hybrid fungal tissue. This method includes the steps for forming an inoculum, which includes a preselected fungus, to form a mixture of a substrate of discrete particles and a nutrient material that is capable of being digested by the fungi. The inoculum is added to the mixture and allows the fungus to digest the nutrient material in the mixture over a period of time sufficient to grow hyphae. The hyphae form a network of interconnected mycelia cells through and around the discrete particles to form a self-supporting composite material. This self-supporting composite material is heated to a temperature sufficient to kill the fungus or otherwise dried to remove any residual water to prevent the further growth of hyphae. The method allows for placing the mixture and inoculum in a mold of any desired shape so that the finished composite material takes on that determined form. The downside to this system is that the fungus must colonize its substrate and incorporate into a solidified form within its carrying mold, limiting production speeds and utilizing one mold per manufactured unit. This method is not conducive to the demands of fast throughput manufacturing and processing that will be needed to make this an economically competitive material.

There are several other methods that have been developed to grow fungus from agricultural and wood industry by-products, using aerated fungal foams, liquid aggregates and the inclusion of secondary reinforcing particles, fibers and other ingredients to aid in making stronger, more resilient materials. Such methods introduce the fungal inoculum into an aerated growth medium, which may include other additional materials such as nutritional supplements or binding and filling agents. The fungal inoculum grows through the foam and binds together its included ingredients into a dense yet flexible material once it has been cured and dried. In one example the method uses different growth mediums such as microcrystalline cellulose mixed with water and nutrients as a support substrate through which the fungal hyphae grow, and as a result rendered into a constituently solidified artifact. After a drying and curing process these fungal foams that include added particles and fibers exhibit increased mechanical strength and flexibility and have other beneficial qualities. This method is limited in application as the size with which one might construct individual components is restricted in volume and mass to small things (2" cubed). While fungal components may be grown together into larger composite pieces, substrate thickness is usually limited to 6" in depth due to the anaerobic conditions can arise in samples that are too dense to allow the free exchange of permeable gases between the fungal substrate and the environment it is growing within. This condition gives rise to anaerobic zones within the fungal substrate, making it susceptible to infection by microbes that favor these types of environments. Thus, most of these cured fungal foams that include particles and fibers are limited to being grown in parts that are too small for use in home construction and many other industrial applications.

The environmental benefits of utilizing fungus for the growth of building blocks and other manufacturing materials might be significant in consideration of the impact and potential use of agricultural waste. As a byproduct of growing and producing food worldwide, humans create a vast amount of agricultural waste that would otherwise be unused, returning vast quantities of carbon and other materials during degradation and decomposition. Such agricultural waste may be viewed as food for a fungus. Hence, it can be seen, that there is a need for developing environmentally friendly materials that might replace traditionally used non-biodegradable durable and strong materials, such as plastics and composites. This method would create stronger and dense building blocks, which can be easily molded and cheaply preprocessed to precise geometric specifications. In addition, this method would make it possible to construct highly complex, structured building blocks which might be arranged and joined with each other to comprise structurally engineered manufacturing components and larger artifacts on the scale of buildings from environmentally friendly materials. More importantly, the building blocks created through this method may be completely biodegradable.

While the above benefits are apparent there is also a need for simplification in the prior art. There is a further need to increase performance of the finished product, such as adhesion strength, and compressive capabilities—all without increasing the weight of the material.

The Applicant has discovered that the application of compressive pressure at points throughout the process, either to the lignocellulose based medium or the growing fungal mycelium, results in vastly increased strength, durability and adhesion characteristics. This process additionally speeds production time and allows for the creation of much larger fungal objects.

SUMMARY OF THE DISCLOSURE

The present invention provides a method for growing organically derived building materials in the form of a moldable substrate which can be engineered to serve a wide range of manufacturing and construction applications.

The present invention discloses obtaining a lignocellulose based medium that is conducive towards the growth of fungal vegetative growth, mixing said lignocellulose based medium with water until a desired hydration level is reached, optionally pasteurizing said lignocellulose based medium, and inoculating said lignocellulose based medium with fungal inoculum and allowing time for said inoculated lignocellulose based medium to become colonized to the extent that said inoculated lignocellulose based medium is permeated with fungal mycelium without any secondary organisms displacing the process through unwanted infection.

During the vegetative growth of the fungal mycelium it is important to maintain an environment and conditions that are conducive to the organism's growth patterns. Thus, the area the fungi are growing within will take into consideration the provision of favorable temperatures, light levels, humidity and gas exchange and other factors, while also protecting the growing fungal mass from infectious agents and organisms that might consume its cells and tissues.

The above steps may occur within a vessel or alternatively on a flat surface, such as a table or conveyer belt, and even after the hydrated substrate has been formed into a condensed and pressed form. The lignocellulose-based medium may be placed into a mold so that the colonized fungal substrate forms into a molded fungal shape. In each case, a primary compressive pressure of at least 100 PSI and preferably at least 500 PSI is applied to the lignocellulose-based medium or colonized fungal mycelium before being reduced by a factor of at least 4 and preferably 20. Secondary and tertiary pressures may be applied throughout the process.

Compression confers vast improvements in the fungal material's ability to withstand dynamic forces, with observations of improvements a factor and better against controls. Compressive strength was found to be 6× over non-compressed, and flexural strength up to a factor.

In another aspect of the present invention, in accordance with the present invention is a method for growing organically derived building materials in the form of a moldable substrate which can be engineered to serve a wide range of manufacturing and construction applications.

A first objective of the present invention is to provide a durable industrial grade material that may serve a wide range of manufacturing and construction applications.

A second objective of the present invention is to provide stronger and more complexly engineered structured blocks for use in industrial and building applications.

A third objective of the present invention is to provide a fungal substrate, which could be molded, and easily and cheaply preprocessed and finished to precise geometric specifications.

Yet another objective of the invention is to provide a plurality of fungal molded shapes in which layers of structural reinforcements or facings may be incorporated to improve load bearing and other structural capacities.

Still another objective of the invention is to provide building materials that are fire resistant, water resistant, and mold resistant, are good insulators and other beneficial properties.

These and other advantages and features of the present invention are described with specificity so as to make the present invention understandable to one of ordinary skill in the art.

BRIEF DESCRIPTION OF THE DRAWINGS

In order to enhance their clarity and improve understanding of these various elements and embodiments of the invention, elements in the figures have not necessarily been drawn to scale. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below. Finally, many of the steps are presented below an order intended only as an exemplary embodiment. Unless logically required, no step should be assumed to be required earlier in the process than a later step simply because it is written first in this document.

Figure 1:
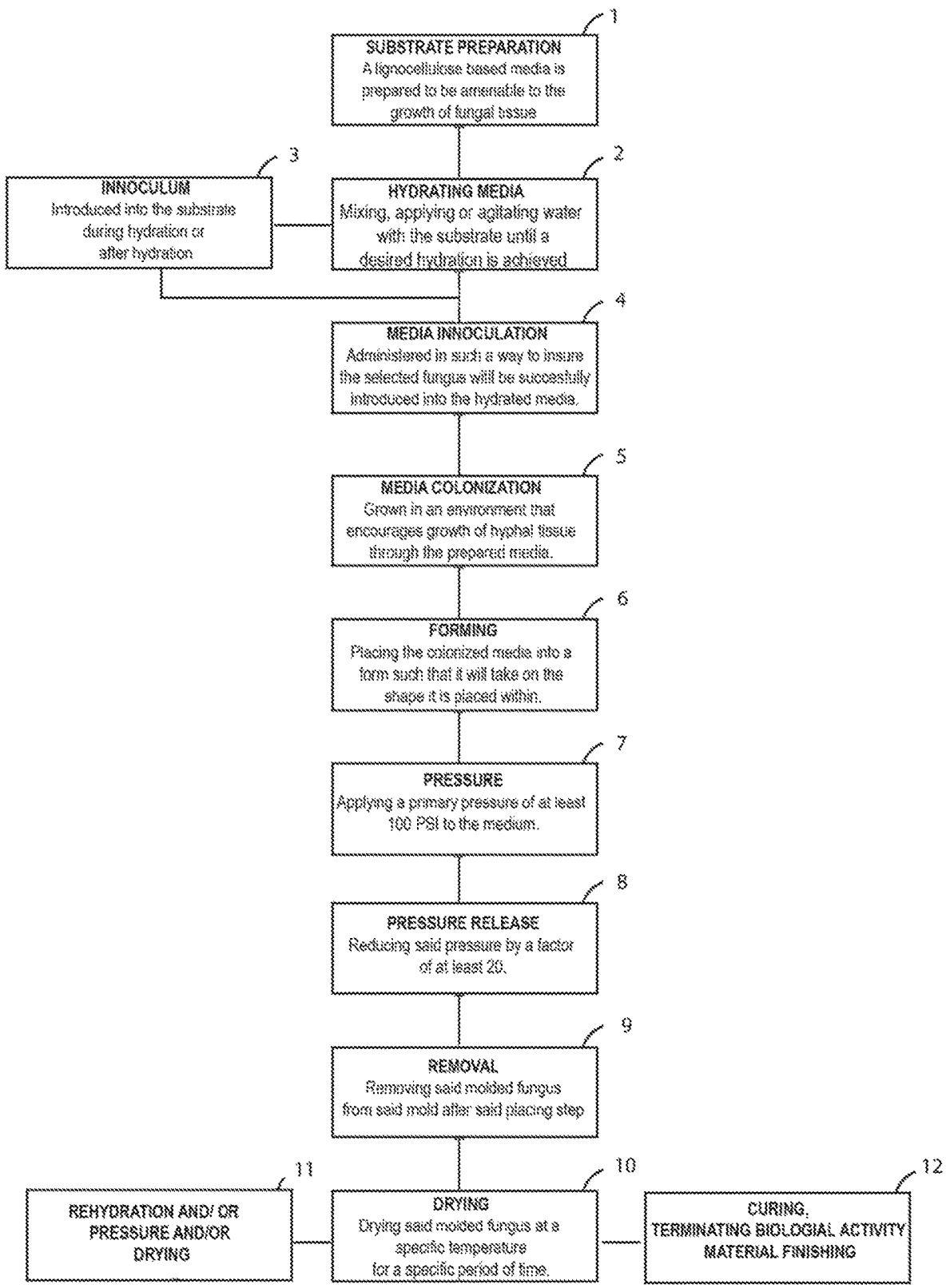
FIG. 1 is an exemplary and preferred embodiment of the method for growing organically derived building materials in the form of a moldable substrate which can be engineered to serve a wide range of manufacturing and construction applications.

An exemplary embodiment of the present invention considers a method for growing organically derived building materials in the form of a moldable substrate which can be engineered to serve a wide range of manufacturing and construction applications. Referring to FIG. 1, an operational flow chart of the method for growing organically derived building materials in the form of a moldable substrate which can be engineered to serve a wide range of manufacturing and construction applications is illustrated. Initially, a lignocellulose based medium that is conducive towards the growth of fungus is obtained, as shown at block 1. One conducive and capable of growing said fungi will have proper amounts of micronutrients, nitrogen, trace elements, and/or vitamins as is known in the art. If said amounts are not present, they may be added to said lignocellulose based medium. Said lignocellulose based medium is mixed with water until a desired hydration level is achieved as indicated at block 2. As an example of steps in this invention that may be taken in any order unless logically required, water may be mixed with said lignocellulose based medium at the same time that micronutrients, nitrogen, trace elements and/or vitamins are added, or even after. Said lignocellulose based medium may be pasteurized for a specific time. After, during, and/or before pasteurization, introduction of a fungal inoculum to the lignocellulose based medium is initiated, as shown in block 3. Then, as indicated at block 4, the selected fungus is allowed to be successfully introduced into the hydrated media. Time is allowed for the inoculated lignocellulose based medium to become colonized to the extent that the inoculated lignocellulose based medium is permeated by fungal mycelium without any secondary organisms displacing the process through infection, as shown in block 5. Colonization is complete enough that secondary organisms are unable to displace this process through infection.

In this embodiment a vessel is provided in which colonization may occur. The fungal mycelium may be placed into a mold so that the fungal mycelium forms into a fungal molded shape as shown and described in block 6. In this method, a primary compressive pressure of at least 100 PSI (and more preferably at least 500 PSI, and in other cases at least 2000 PSI) is applied to the fungal mycelium as shown in block 7. In other embodiments, said primary compressive pressure can be at least 100 PSI. The amount of time the pressure is applied and the step at which pressurization occurs are variable. For instance, primary compressive pressure may be applied at any of the steps prior to inoculation. Preferably, however, and in this embodiment, the primary compressive pressure is placed on the fungal mycelium as it is in the mold. Said primary compressive pressure is then reduced by a factor of at least 4, but preferably at least 20 as indicated at block 8. In a preferred embodiment pressure is reduced to ambient environment pressure, which at sea level at 15 degrees Celsius is 760 mmHg, or around 14.696 PSI. Said fungal molded shape is removed from said mold after said placing step as shown in block 9. As indicated at block 10, said fungal molded shape is dried at a specific temperature for a specific time period. Steps shown in blocks 11 (rehydration and/or pressure and/or drying) and 12 (curing, terminating biological activity, material finishing) are described in detail later in this document.

Figure 12:
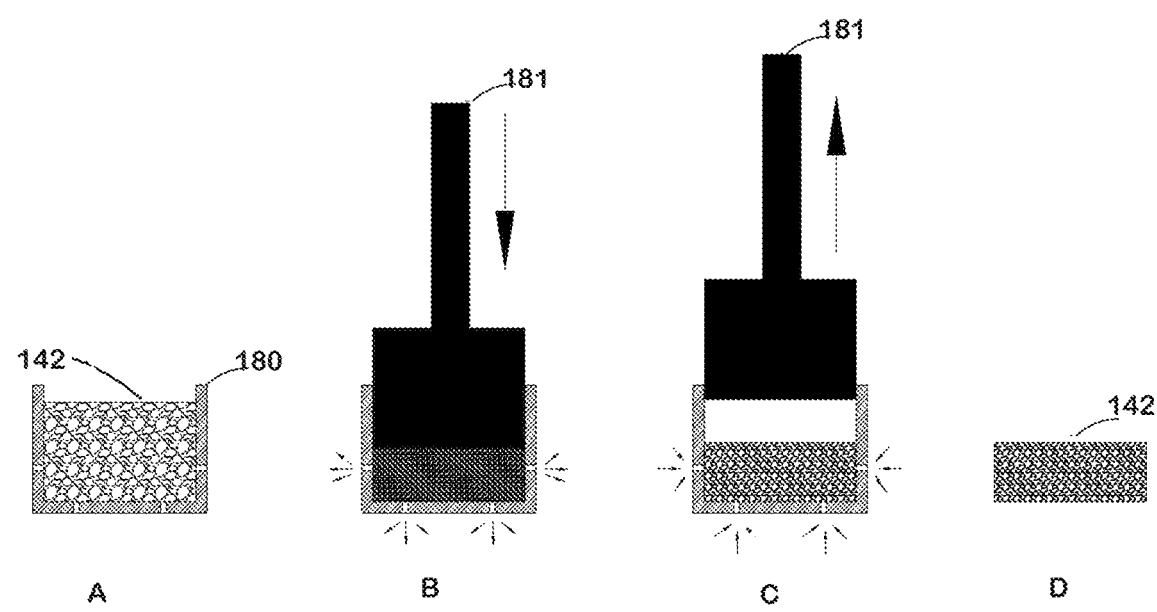
FIG. 12 includes four images taken as steps in a process from left to right, wherein a vessel is depicted holding a fungal molded shape, then a piston is shown compressing said shape such that outgassing occurs, then upon release of the piston ingassing is apparent as the shape naturally rebounds to some extent, resulting in the final image on the right hand side of the figure.

In this method, the fungal molded shape forms the organically derived building material. The environmental conditions in the vessel are regulated by providing a regulatable relationship between said vessel and the outside environment, as described below. The lignocellulose-based medium is mixed with water to provide a sufficient amount of water to adequately hydrate the lignocellulose-based medium. The pasteurizing step, if present, should be terminated subsequent to the termination of said mixing step. The lignocellulose substrate base may be pasteurized using heat pasteurization and the vessel may be cooled subsequent to said pasteurizing step. The method also provides a buffer to balance the pH of the lignocellulose-based medium. The fungal inoculum allows the growth of the tissue of the selected fungus to be administered through, in, or on the lignocellulose substrate. In addition, a secondary compressive pressure, at least 100 PSI, is applied to the fungal molded shape after the fungal molded shape is removed from the mold. The secondary compressive pressure may be physically applied using any suitable means, such as a compressive piston or a roller such as a stationary roller on a moving conveyer belt holding the fungal molded shape. The secondary compressive pressure is then released and then a tertiary compressive pressure of at least 100 PSI may be applied to the fungal molded shape. Additional increases and decreases of pressure are optional. The pressure may be sufficient to cause saturated water within the fungal molded shape to be forced out, thereby allowing the fungal molded shape to absorb an agent, either fluid or gas, as shown in FIG. 12 and described in the accompanying text. The method may be further accompanied by pulverizing said fungal molded shape into a plurality of small pieces. As with many steps in this process, pulverization does not necessarily occur either before or after any other compression step.

Figure 2:
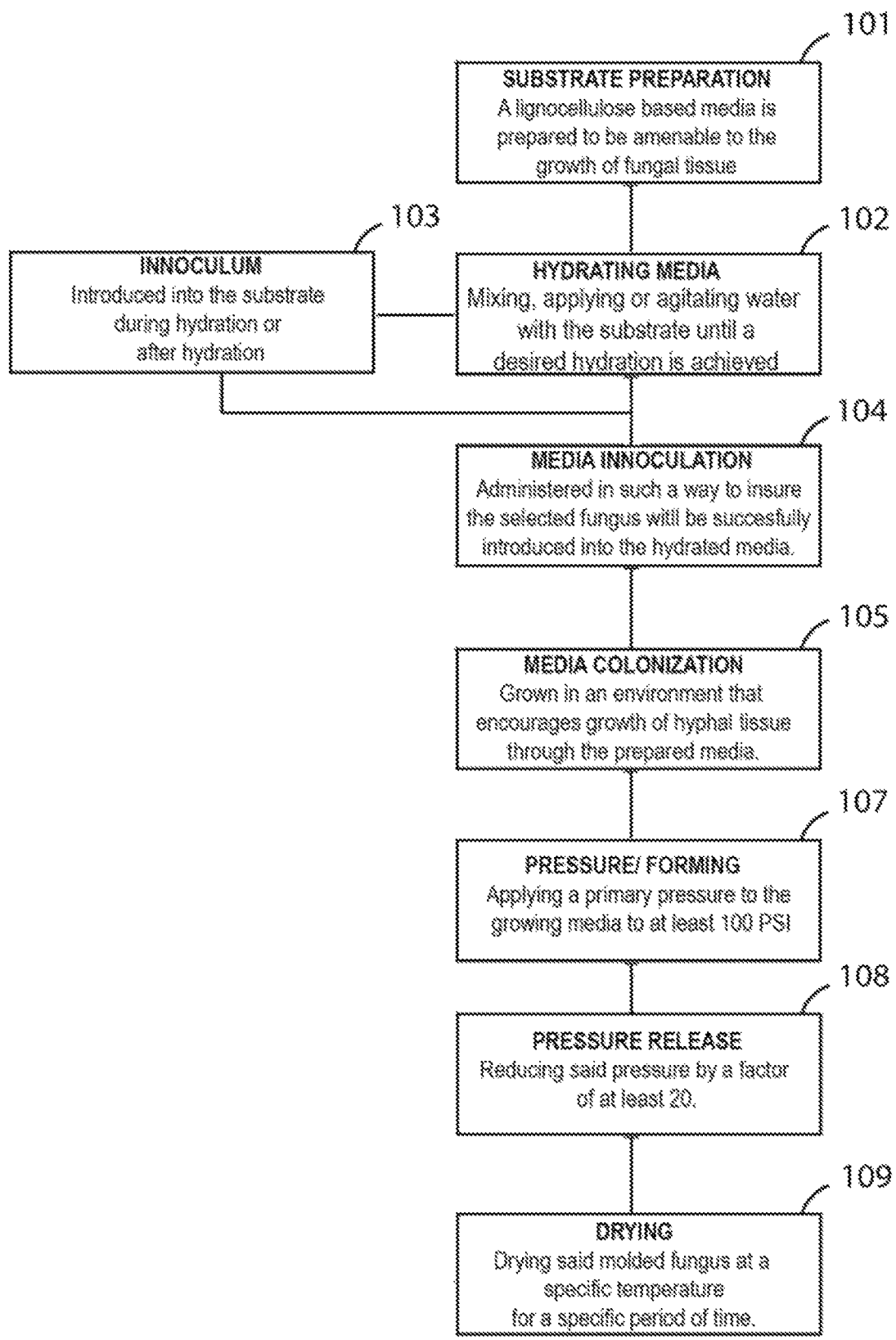
FIG. 2 is an exemplary and alternative operational flow chart of a method for growing organically derived building materials in the form of a moldable substrate which can be engineered to serve a wide range of manufacturing and construction applications in accordance with the present invention.

Turning now to FIG. 2, an operational flow chart for a method for growing organically derived building materials in the form of a moldable substrate which can be engineered to serve a wide range of manufacturing and construction applications in accordance with an aspect of the exemplary embodiment of the present invention is illustrated. Initially, a lignocellulose based medium that is conducive towards the growth of fungus is obtained, as shown at block 101. One conducive and capable of growing saprophytic fungi will have proper amounts of micronutrients, nitrogen, trace elements, and/or vitamins as is known in the art. If said amounts are not present, they may be added to said lignocellulose based medium. Said lignocellulose based medium is mixed with water until a desired hydration level is achieved as indicated at block 102. Preferably, the hydration level is approximately 66%. That is, the total weight after hydration is composed of 2 parts water for every 1 part lignocellulose based medium. Other options might include a range of 33-66% hydration, and in some cases, 25-75%.

Said lignocellulose based medium may optionally be pasteurized for a specific time. Whether pasteurized or not, the lignocellulose based medium may be inoculated with a fungal inoculum 103 to create a fungal mycelium such that the tissue of the fungal inoculum grows through and fully colonizes said fungal mycelium as shown in block 104. In this method time is allowed for said inoculated lignocellulose based medium to become colonized to the extent that said inoculated lignocellulose based medium is transformed into a fungal mycelium without any secondary organisms displacing the process through infections, as indicated at block 105. Then, environmental conditions surrounding the inoculation process are strictly regulated and the fungal mycelium is allowed to grow.

A pressure is added on the growing fungal mycelium to at least 100 PSI as shown in block 107. In this method, a primary compressive pressure of at least 500 PSI is applied to the fungal mycelium. In other embodiments, said primary compressive pressure can be at least 100 PSI. The amount of time the pressure is applied and the step at which pressurization occurs are variable. For instance, primary compressive pressure may be applied at any of the steps prior to inoculation. Preferably, however, and in this embodiment, the primary compressive pressure is placed on the fungal mycelium as it moves down on a continuous feed system, such as a conveyer belt of assembly line. Pressure may be applied through a mechanical press, roller, or other suitable compressing means used in continuous feed systems. The applied pressure on the growing fungal mycelium is reduced as indicated at block 108, preferably by a factor of 20, and less preferably by a factor of at least 4. Preferably, pressure is set at ambient environmental pressure as described above with regard to the first embodiment. Said colonized fungal mycelium is dried for a specific time period as shown in block 109. The method may be further accompanied by pulverizing said fungal mycelium into a plurality of small pieces. As with many steps in this process, pulverization does not necessarily occur either before or after any other compression step.

As with the first embodiment described above, a secondary compressive pressure, at least 100 PSI, may be applied during this process. This may occur before or after drying. The secondary compressive pressure may be physically applied using any suitable means as described above in this embodiment and with regard to the first compressive pressure. The secondary compressive pressure is then released and then a tertiary compressive pressure of at least 100 PSI may be applied to the fungal molded shape in the same manner. Additional increases and decreases of pressure are optional.

Any of the first, second, third, compressive pressures may be sufficient to cause saturated water within the fungal molded shape to be forced out, thereby allowing the fungal molded shape to absorb an agent, either fluid or gas, as shown in FIG. 12 and described in the accompanying text.

Figure 3:
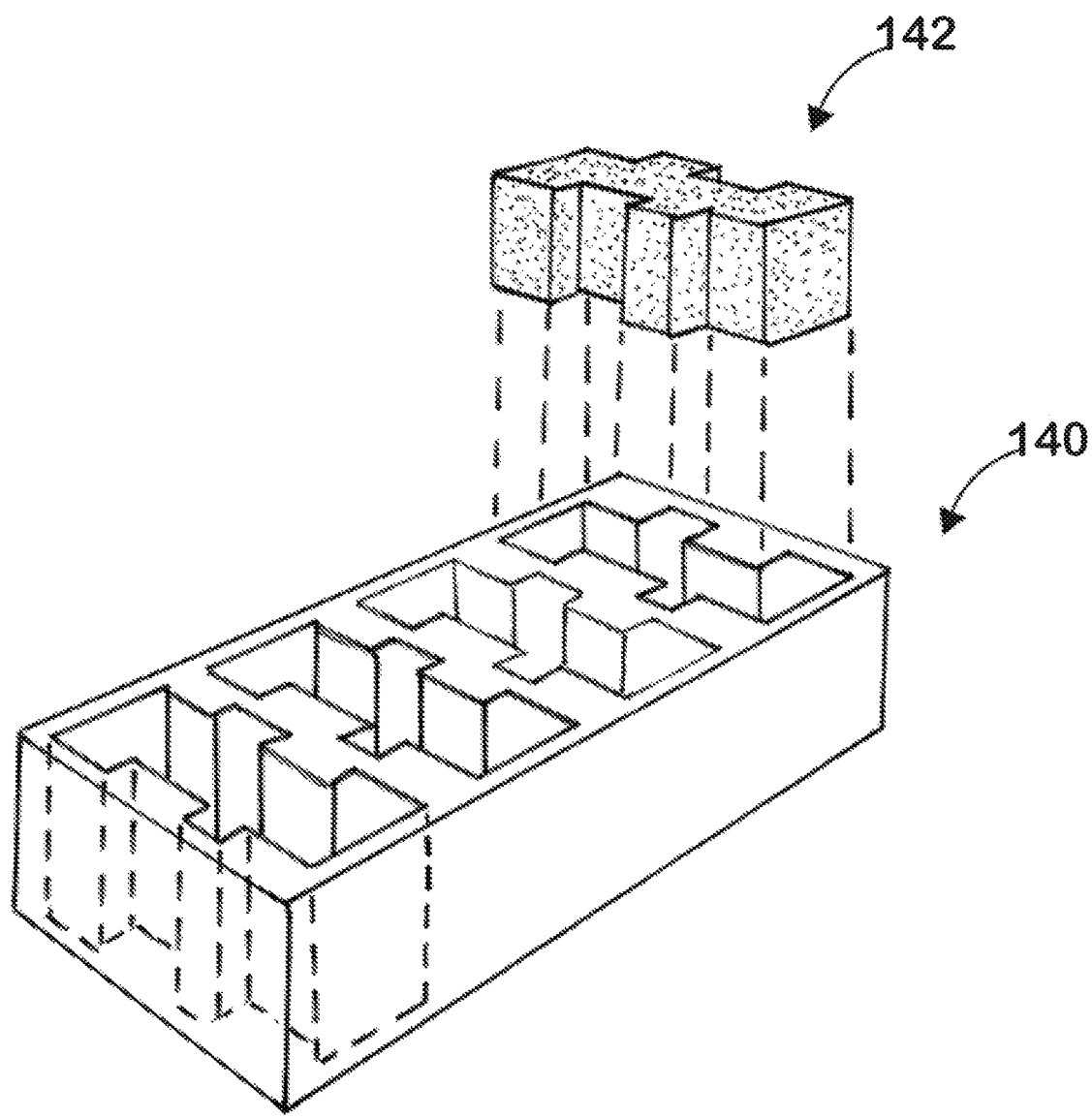
FIG. 3 illustrates a mold used to form a fungal molded shape in accordance with the exemplary embodiment of the present invention.

FIG. 3 illustrates a mold 140 used to form an example fungal molded shape 142 in accordance with the exemplary embodiment of the present invention. In this exemplary embodiment, the fungal mycelium forms a fungal molded shape. The vessel is kept in a growing room having a temperature of between 55 and 90 degrees Fahrenheit. The vessel may be of nearly any volume, including containers such as a large room or an entire building, and may be either rigid or soft and flexible. The hard vessel may be a thermoplastic mold and the soft vessel may be a bag made of plastic or polyethylene. The use of thermoplastic molds allows for more complex geometries, greater consistency in shape of the produced blocks, and larger forms. The growing room should have a regulatable environment as far as ambient and desired gas levels are concerned ($O^2$, $CO^2$, etc.), temperature, humidity and light levels. The environmental conditions of the growing room are regulated by providing a regulatable relationship between the vessel and outside environment. During the vegetative growth of the fungal mycelium it is important to maintain an environment and conditions that are conducive to the organism's growth patterns. Thus, the area the fungi are growing within will take into consideration the provision of favorable temperatures, light levels, humidity and gas exchange, while also protecting the growing fungal mass from infectious agents and organisms that might consume its cells and tissues.

The vessel may comprise a flexible breathable filter membrane or flexible breathable filter membrane patch to allow for gas exchange while preventing unwanted bacteria and microorganisms from infecting said growing fungal substrate. When the fungal inoculum has fully colonized the contents of the mold, the fungal molded shape is solid enough to take out of the mold 140. The lignocellulose-based medium is placed into the mold 140 so that the colonized fungal substrate forms into a fungal molded shape. The mold 140 may be selected from a group consisting of a wooden mold and a thermoplastic mold. Next, the plurality of fungal molded shapes is dried using any known method for drying structures. In one embodiment, placing the fungal molded shapes in an 80-90 degrees Fahrenheit areas and using dehumidifiers and fans to accelerate the process is used. Drying may be accompanied by dehydration of the fungal molded shape such that water weight of said fungal molded shape is at most 15% of the total weight of said fungal molded shape. Drying with heat may make the fungal inoculum biologically inert. Other methods for drying involve chemically killing the fungal mycelium (through any known biocide, fungicide, alcohol etc.), microwaves, or even smoking. In the smoking process, the fungal mycelium is dried and cured similarly to the common process for flavoring, cooking, or preserving foodstuff. Drying may also be done in conjunction with continuous or pulsed application of linear pressure, which would result in a thinner and denser building material. This type of drying may be employed for the manufacture of consumer electronics such as phone casings. This process may be used in combination with others described in this patent application, such as the uptake of agents through compression and natural re-expansion.

Figure 4:
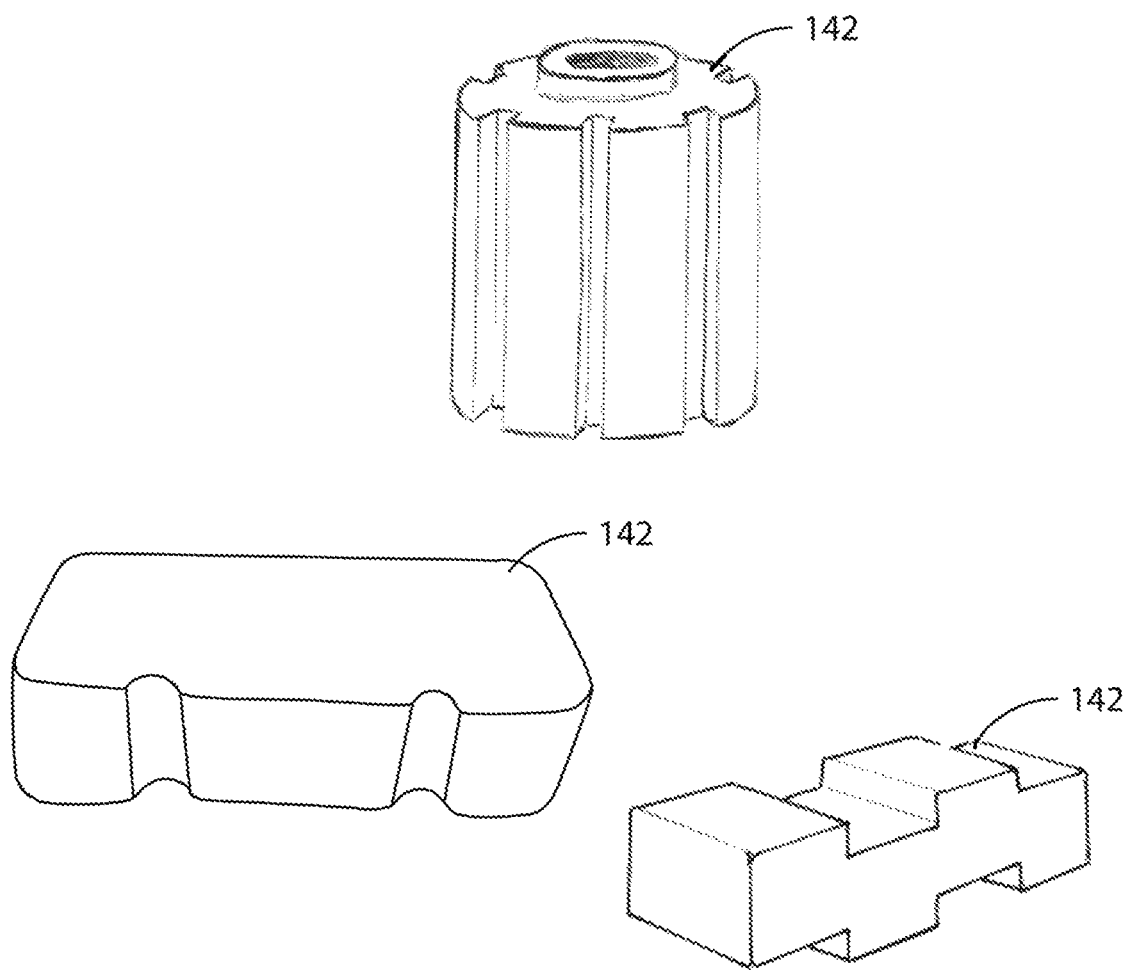
FIG. 4 illustrates a plurality of fungal molded shapes formed by the mold in accordance with the exemplary embodiment of the present invention.

FIG. 4 illustrates a plurality of fungal molded shapes 142 formed by the mold 140 in accordance with the exemplary embodiment of the present invention. When the fungal inoculum has fully colonized the contents of the mold, the plurality of fungal molded shape 142 is solid enough to take out of its mold. At this point, the fungal molded shapes 142 may be dried as individual fungal molded shape, or placed in proximal contact with one another such that an organic bond forms between each of the plurality of fungal molded shapes 142. Each of the plurality of fungal molded shapes 142 comprises an outer surface of mycelium, and wherein each said outer surface fuses with the other to form an organic bond. The surface of the fungal molded shapes 142 forms a skin during colonization. The properties of this skin, such as consistency, strength, and density, may be manipulated by changing temperatures, light levels, gas concentrations, and photo periods during the colonization period and after for any continued length of time. The fungal inoculum may be a compressed form of mycelium fungi. The fungal inoculum may be selected from the group consisting of: *Ganoderma lucidem, Ganoderma tsugae, Ganoderma oregonense, Fomes fomentarius, Trametes versicolor* and *Piptoporous betulinus*. The colonized or uncolonized substrate is combined with materials to change qualities and attributes of the growing fungus and the substrate composition. The materials for combining may be selected from the group consisting of silica, perlite, methylcellulose, glycerin, agarose, or any other materials that retain liquids through hydrophilic carrying capacities and demonstrable qualities of enhanced or desirable viscosity. Preferably the materials are all inert cellular material and retain liquids through hydrophilic carrying capacities and demonstrable viscous qualities.

Figure 5:
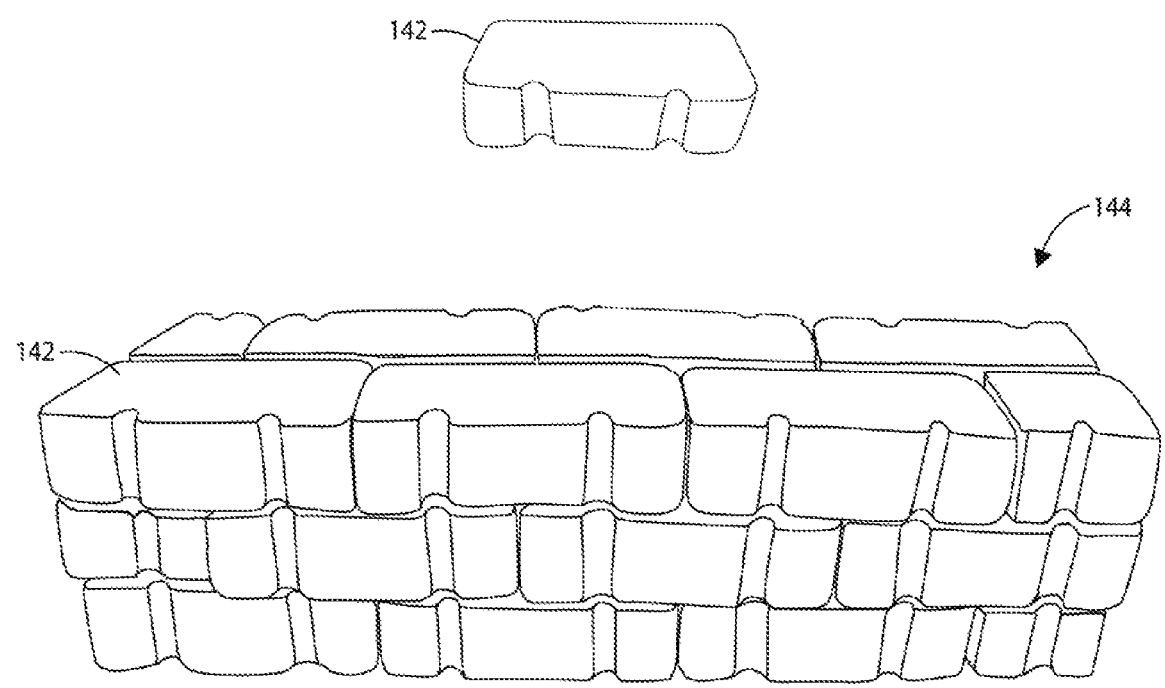
FIG. 5 illustrates the plurality of fungal molded shapes assembled together in a wall formation, wherein one exemplary brick is depicted apart from the wall.

FIG. 5 illustrates the plurality of fungal molded shapes 142 assembled together to make a larger structure 144 in accordance with the exemplary embodiment of the present invention. The fungal molded shapes 142 may be joined together to make larger structure 144. It is possible to fabricate a wide set of complexly assembled structures from a modular vocabulary of interlocking forms. Adhesion between individual fungal molded shapes can be engineered for specific interfaces and connections, with defined planes, edges, bevels, mounts, or other fixturing elements that may distribute forces between and amongst conjoined modules. Once assembled, these forms may organically weld to one another to create even more complex structural assemblies, as described below.

Silica, perlite, clay and other biologically inert materials may be added to the lignocellulose substrate in order to change material qualities that include density, porosity and flexural capacities. After being dried, the material becomes more resilient if treated with a wax, oil or other types of available sealants. The fungal molded shapes 142 derive their particular strength from the density of mycelial mass can also be effected by the thickening of the substrate skin. These qualities can be achieved through many factors, one being the gas levels ($O^2$, $CO^2$, etc.) in the immediate growing environment of the growing fungus. The addition of selected molds, algae or other microorganism to the immediate environment in which the fungus is growing creates a condition in which the growing fungal substrate forms a tough skin or "blister" on its surface, and otherwise become much denser as a reaction to the secondary gases and metabolites produced from said added organisms. Fungal bricks grown in association with algae exhibit the habit of growing rhizomorphic formations, wherein a tough, hardened casing is generated, and is similar to thermoplastics in hardness and durability. Rhizomorphs are large, tubular collectives of hyphal cells, which form thick parallel strands of in fungal mycelia, which upon drying resemble the shells of beetles and other insects who comprise their exoskeleton from densely woven chitin.

Continuing with FIG. 5, the exemplary block shown above may optionally be combined with secondary materials. In certain embodiments, the fungal mycelium is allowed to grow into a laminate surface, or optionally a laminate surface is affixed to dried fungal mycelium, through any suitable means such as glue. The laminate may serve to protect the fungal surface from natural decomposition, may offer increased strength when a sheet of laminate is placed between two fungal mycelium surfaces, and can serve to prevent an active mycelium to mycelium relationship between two surfaces that without the laminate would otherwise be in contact. Additional layers of fungal mycelium may be joined together, each with laminate between them, to offer additional qualities, such as high impact resistance and bulletproofing.

Figure 6:
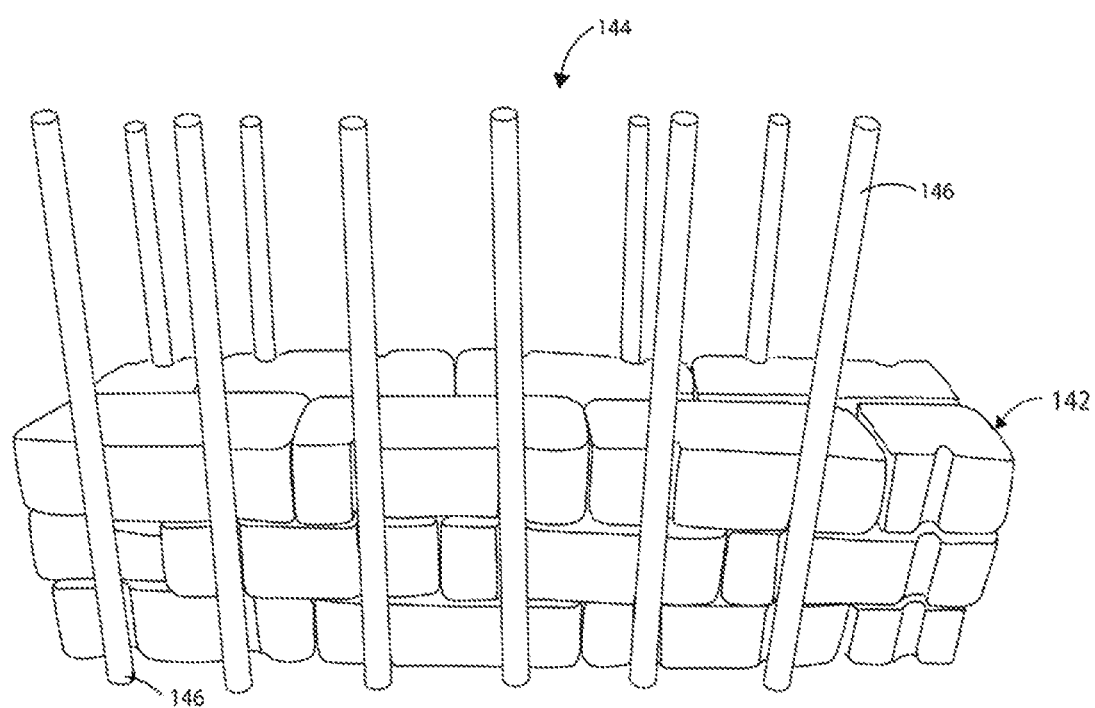
FIG. 6 illustrates the plurality of fungal molded shapes incorporated with a plurality of dowels to create structural connections in accordance with the exemplary embodiment of the present invention.

FIG. 6 illustrates the plurality of fungal molded shapes 142 incorporated with a plurality of dowels 146 to create structural connections in accordance with the exemplary embodiment of the present invention. The plurality of dowels 146 may be cross-linked with wire or other binding materials, compressing the fungal molded shapes 142 together. The dowels 146 act as a registration system as well as materials for facing or skinning. Bamboo, steel, or any other tensile materials may be used instead of wood dowels. In this case, a double layer of fungal molded shapes are stacked offset, with the guiding channels in the fungal molded shapes holding dowels in place.

Figure 7:
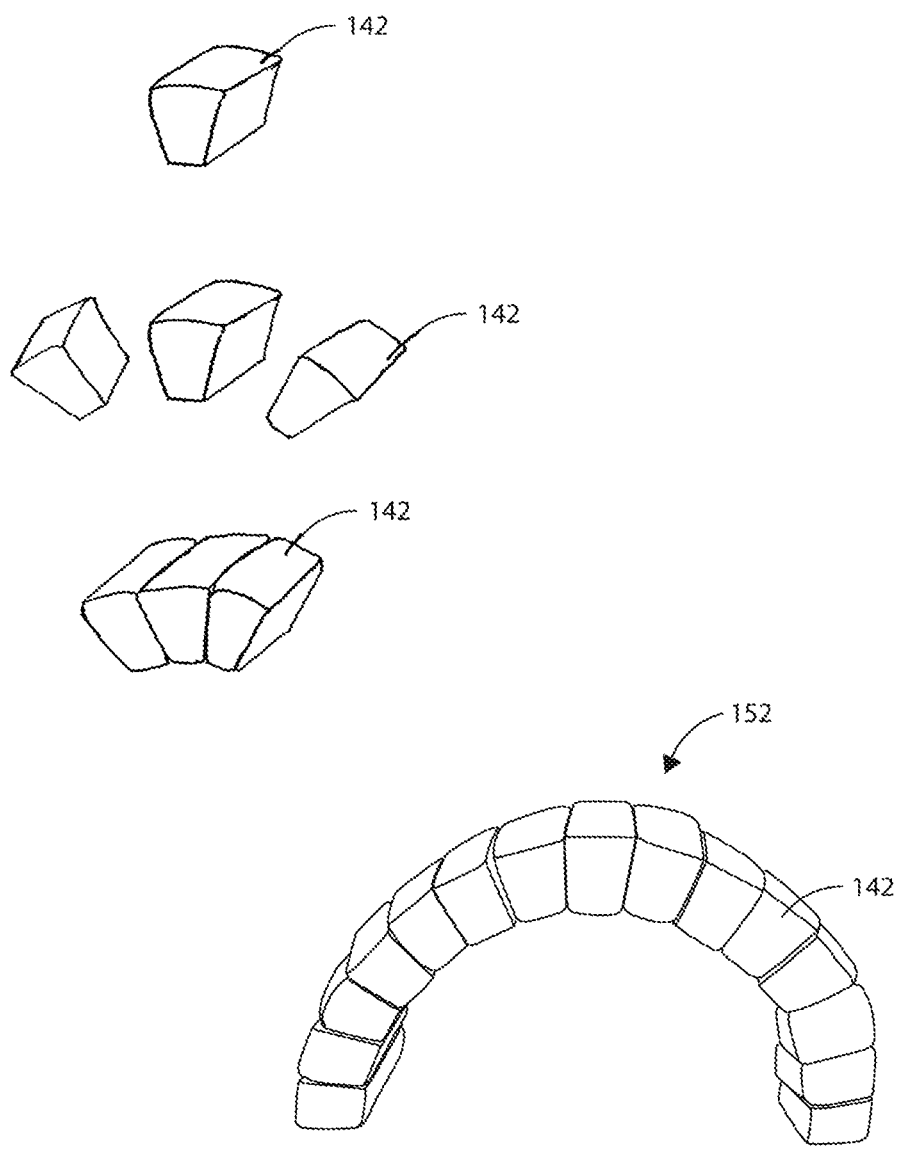
FIG. 7 illustrates a the construction of an archway formed by placing the plurality of fungal molded shapes in proximal contact with one another to form an organic bond in accordance with the exemplary embodiment of the present invention.

FIG. 7 illustrates the creation of an arch 152 by placing the plurality of fungal molded shapes 142 in proximal contact with one another to form an organic bond in accordance with the exemplary embodiment of the present invention. The fungal molded shapes 142 formed into a complex composite shape utilizing the organic weld. The fungal molded shapes may also be joined to form a structure in the form of the arch 152. The fungal molded shapes 142 may be joined together and adhered to one another to form an organic weld between any given numbers of fungal molded shape 142. Sticking two fungal molded shapes 142 is accomplished by stationing one on top of the other while the material is still alive, that is, before it has dried out. Once connected, the fungal molded shapes may be left alone in a nominally controlled environment, until a strong bond is formed. Although the fungal molded shapes 142 shown in the exemplary embodiment take the form of individual shapes, a set of fewer or more blocks can similarly be used to form a structure. Fewer blocks makes for a simpler system, reducing the number of casts that must be made, while a greater number of blocks allows for greater customization and variation in design.

Figure 8:
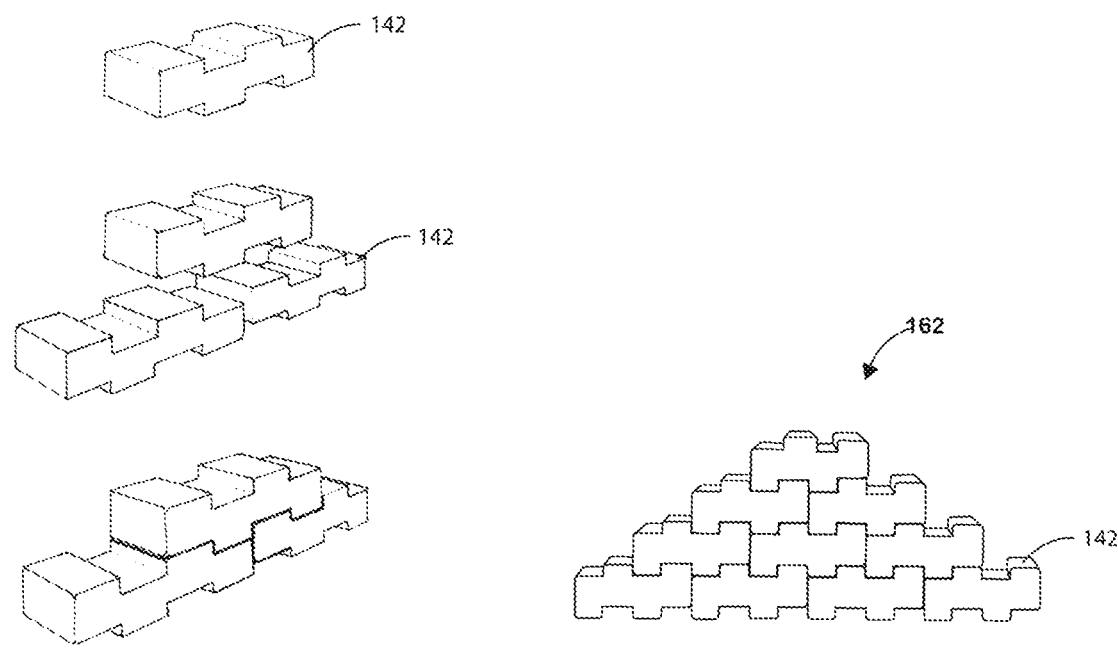
FIG. 8 illustrates the construction of a wall like structure formed by placing the plurality of fungal molded shapes in proximal contact with one another to form an organic bond in accordance with the exemplary embodiment of the present invention.

FIG. 8 illustrates the creation of a wall portion 162 by placing the plurality of fungal molded shapes 142 in proximal contact with one another to form an organic bond in accordance with the exemplary embodiment of the present invention. The fungal molded shapes 142 formed into a complex composite shape utilizing the organic weld. The fungal molded shapes may also be joined to form a structure in the form of a wall, a portion of which is shown as wall portion 162.

The organic welding is accomplished by action of the fungus itself. If grown in optimized conditions, the fungus may be induced to fuse with any cloned mass of its own tissue. This is well known, and described in U.S. Pat. No. 5,074,959 to Yamanaka. By virtue of this fusing property of the fungus it is possible to manufacture building elements that are designed to fuse together, which after drying may be machined, treated, and formed as one might a wood or composite board. The method disclosed by the current application forms the fungal molded shapes 142 in such a way as to maximize surface contact with any fungal molded shape, which facilitates and encourages the fusing process. The process of fusing fungal molded shapes 142 together simply requires stacking individual forms in a manner such that there is direct surface contact between the discrete forms. Environmental factors may be altered to affect the speed and quality of the organic weld. These environmental factors may include photo periods, temperature, moisture levels, and suppression of the ambient microbial life in the growing space. Fast duration compaction of precolonized substrate may result in a densely packed form that has absorbed an aqueous gel agent deep within the fungal mycelium. This aqueous gel could be seeded with a solution of time release peroxisomic compounds that will induce specific curves of gas concentrations throughout the growing form, enabling a more vigorous mycelia growth rate and reducing the risks of secondary infection by anaerobic microbes.

The density of the mycelium and the material properties of the building materials may be varied by controlling various inputs to the manufacturing process. By controlling these inputs, it is possible to achieve stronger and more finely resolved features in objects composed from this dried somatic substance. These controlling inputs include the size and form of the lignocellulosic ingredients that comprise the substrate material. Different shapes and consistencies of substrate material will alter the composition and qualities of the cultivated objects. Other controlling inputs include the environmental conditions in which the fungi are grown. Increased material densities can also be achieved by mechanically concentrating the substrate in resilient and durable molds, and also through pressing fully colonized living materials into secondary molds to achieve greater material densities and finer resolutions. Living material treated and re-combined in this manner continues to grow, and can be shaped into artifacts with fine resolutions and surface qualities.

Figure 9:
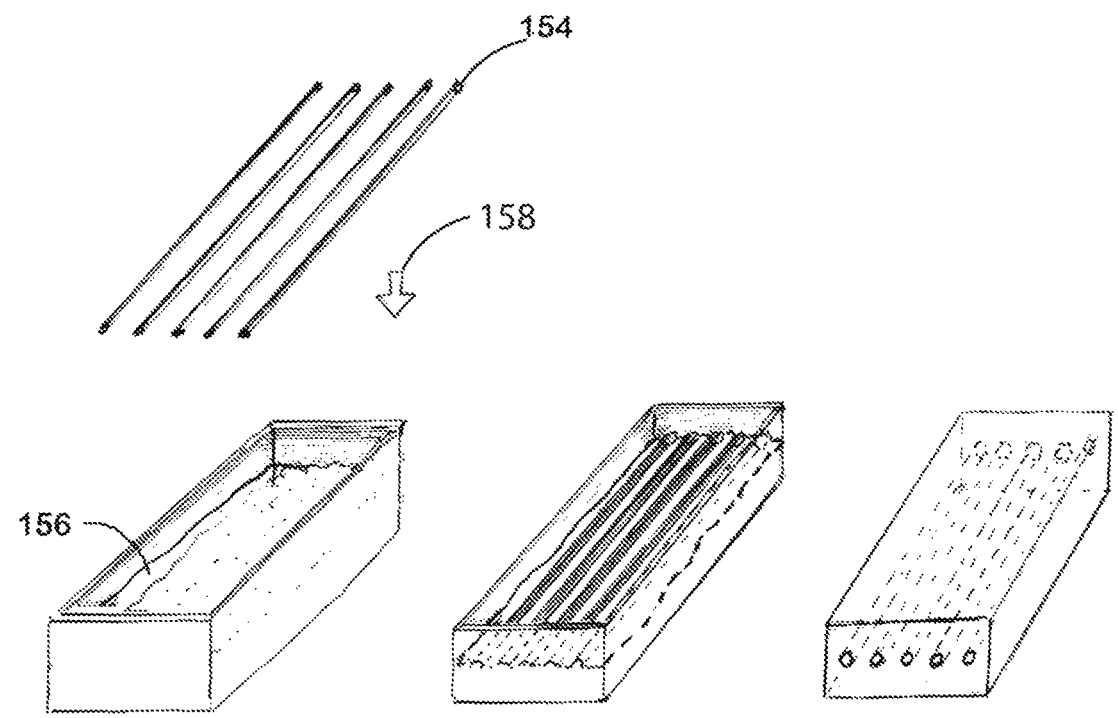
FIG. 9 illustrates secondary materials incorporated into the fungal mycelium to create structural connections in accordance with the exemplary embodiment of the present invention.

FIG. 9 illustrates secondary materials 154 incorporated into the fungal mycelium 156 to create structural connections in accordance with the exemplary embodiment of the present invention. Secondary materials 154 are incorporated into the fungal mycelium 156 to further create structural connections, mechanical reinforcements, and interfacings within and on the surface of the molded fungal shape. These inserted secondary materials can then be incorporated within the living mycelium. The secondary materials 154 may be but are not limited to woven bamboo, sisal and other organic materials. These secondary materials are preferably stacked between the fungal mycelium 156, but may be integrated in using other methods as known in the art. These stacked sheets of secondary materials are then incubated, grown, and fused together with the mycelium. Secondary materials may be inserted partially from one surface to the middle, or can fully pierce the sample along any desired axial path. These layers of thin organic material may be grown together in sheets or pressed and formed into molds with specific shapes. These reinforcements can change skin densities, reinforce adhesion, structurally reinforce assembly components, and create building elements with interfaces and connection points that include incorporated fixturing and fastening elements. The mycelium added to this organic substrate will bond the layers together into a solid laminate.

When pressure is applied such as is shown in FIG. 8 by arrow 158, the bonding becomes even stronger between the secondary materials 154 and the fungal mycelium 156.

In another instance, thin rods and slats of bamboo, rattan, or other material may be layered near the top and bottom surface of the substrate, each set at right angles to the other; and then this cross-grained laminate may be pressed into a secondary form and allowed to grow. The bamboo may also act as a spanning reinforcement, making bricks or other forms that can be load bearing and serve other structural capacities. In another instance, rope or other tensile material may be used to reinforce a structural element. These, and other incorporated elements may change the properties of the dried and finished object, altering the shear and tensile strengths in ways that are similar to the tuning of composite materials. In this way it is possible to design and grow organically derived structural elements, and these elements may be engineered with specific material tolerances and capabilities.

Figure 10:
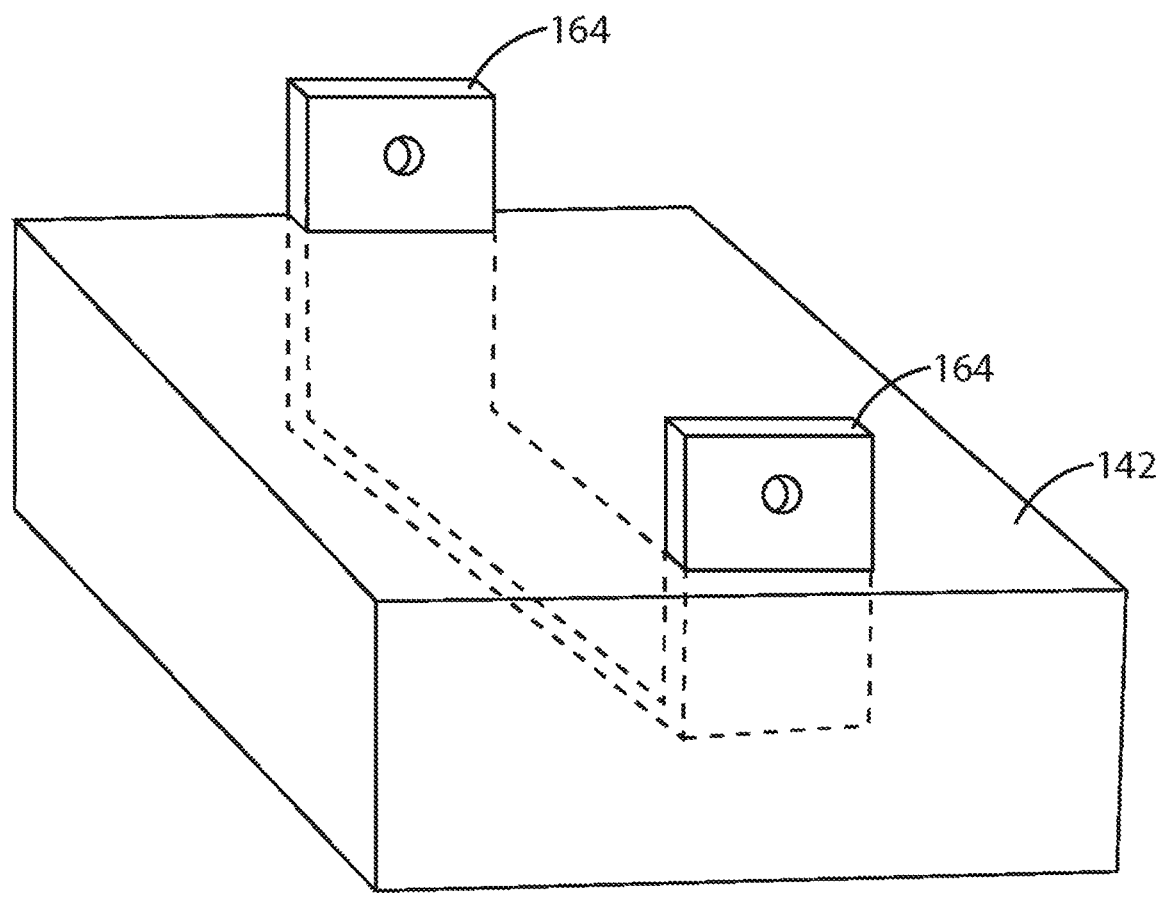
FIG. 10 illustrates a two tab fixturing element incorporated directly into the fungal molded shape in accordance with another aspect of the exemplary embodiment of the present invention.

FIG. 10 illustrates a two-tabbed fixturing element 164 incorporated directly into the fungal molded shape 142 in accordance with another aspect of the exemplary embodiment the present invention. When the compressive forces are applied as exemplarily shown in FIG. 9, the fixturing element 164 becomes even more tightly embedded in the fungal molded shape than would be possible using conventional technology. A grown and dried fungal molded shape 142 of somatic material is incorporated with the two-tab fixturing element 164. The fungal molded shape 142 may be incorporated with the structural elements with portions extending out from the fungal material, and may be designed as an incorporated fastening or fixturing element. The fastening or fixturing elements may include holes, tabs, hoops, locks, pegs, or any other mechanical device for anchoring, connecting or interfacing a fungal object. Through the combination of adding amendments to the substrate and adding structural elements within and between grown and growing fungal molded shapes, various building material properties may be developed. It is to be understood that the disclosed exemplary embodiments are illustrative merely of the concept and general practice of incorporating fastening or fixturing elements, and are not intended to limit the scope of breadth of the claimed subject matter.

In another alternate embodiment where the stronger and denser building blocks are created by use of pressure and the pasteurized substrate is first colonized and allowed to grow until fully colonized, the substrate preferably has a weight ratio of approximately 2 pounds of water per pound of dry weight sawdust, ground nutshells, or corn cobs. After the substrate is fully colonized, it is crumbled and broken apart, filtered by size, and then compressed under pressure into molds of desired shape and size. It is noted that compressing the smallest particles of fungal mycelium using this technique resulted in the strongest material. The broken up and filtered fungal mycelium is compressed with applied pressure between 300-500 psi. If the material is over-compressed, upon decompression the substrate will expand, absorbing air and any other material in the mold. By adjusting the pressure applied, the grain size, and the hydration of the substrate 170 before compression, it is possible to vary the density of the final product and adjust various material qualities. After compression, the material may be left in the mold or may be immediately turned out onto a secondary growth surface. After the compressed material is turned out of its mold, it may require a minimum of three days with proper environmental adjustments for the mycelium to reestablish and connect back together resulting in a strong final product. The turned out material may be allowed more than three days after compression depending upon desired final surface qualities and other tunable variables.

In yet another embodiment, the fungal mycelium is partially dried and rehydrated while undergoing the pulsed application of linear pressure, thereby allowing for a much denser and thinner material than is currently manufacturable, with possible applications replacing high impact.

In association with any of the drying phases, stressing and reforming of the original sample may induce stress fractures, cracks and deformities in the sample. These can then pressed (with or without rehydration) so that the internal mycelium can regrow through these fractures, cracks and deformities, structurally reinforcing the sample. The above can happen without the application of pressure as well.

Figure 11:
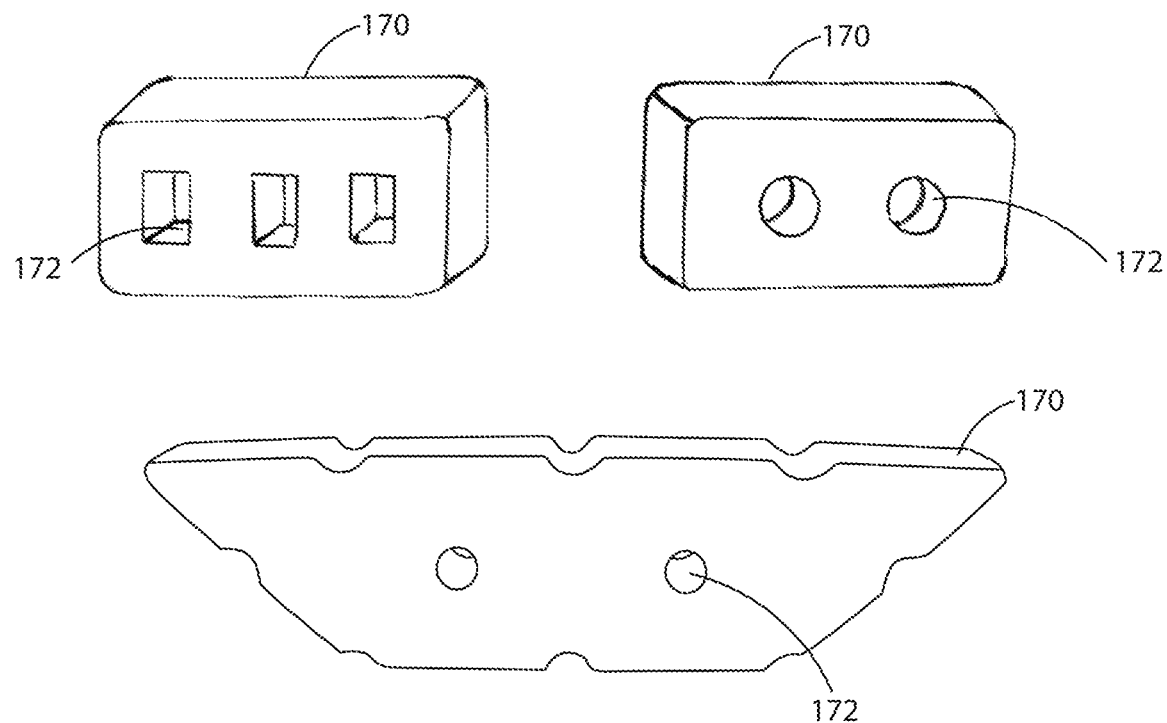
FIG. 11 illustrates a plurality of fungal molded shapes formed with cast void spaces in accordance with the alternate embodiment of the present invention.

FIG. 11 illustrates a plurality of fungal molded shapes 170 formed with cast void spaces 172 in accordance with the alternate embodiment of the present invention. The fungal molded shape 170 may be grown with channels, void spaces, raised features, and registration artifacts capable of coupling the plurality of fungal molded shapes to other objects. By utilizing pressure compression method, it is possible to use one and two part molds with drop pins and void spaces. It would also be possible to construct any type of multiple part molds for compressing the fungal mycelium in this way, similar to the molds used for injection molding. Using this method, it is possible to create beams and other elements of significant size. Additionally, it is possible to combine this high-pressure embodiment with the above-disclosed embodiments, which incorporate additional materials such as bamboo or rope into the final product.

FIG. 12 depicts four images taken as steps in a process from left to right, wherein a vessel 180 is depicted holding a fungal molded shape 142, then a piston 181 is shown compressing said fungal molded shape 142 such that outgassing occurs, then upon release of the piston 181 ingassing is apparent as the fungal molded shape 142 naturally rebounds or expand to some extent, resulting in the final image on the right hand side of the figure. Not shown, if the area around the vessel were surrounded with an agent, either gaseous or liquid, it would be taken up by the expanding fungal form. Importantly, this method allows gas and liquid agents to be introduced to a fungal molded shape without any mechanical injection. Instead, negative pressure from the expanding fungal form causes the form to naturally uptake agents surrounding it. Although in this image a vessel is shown, compression could occur in other manners, such as by a roller as the fungal body moves down a continuous assembly line or conveyer belt. By surrounding the fungal body with the agent (either liquid or gas) immediately after compression is released, the fungal body will uptake the agent.

The above-mentioned partial drying with rehydration that includes suspended liquid/solid/gas/biological agents that may create a protective layer against infection for the mycelium within the sample. Possible applications may be used in growing two bricks together within environments that do not have adequate environmental controls, with the protective layer keeping unwanted living agents from infecting the sample. This protective layer can be rendered inert or permeable to the internal mycelium through the application of water or other hydrating agents. Building on site of complex fungal structures would be possible with this. Suspended agents may include the following as singular agents, in combination, or in successive application: Xanthan gum, Locust bean gum, Guar gum in combination with calcium to form gelling cross links, other commercially available protective food gums, Carboxylmethylcellulose, Carboxylmethylcellulose in combination with potassium sorbate, alcohols of various types, including but not limited to, and in purified or gelled suspensions, calcium, chlorine, chlorophenols, benzalkonium chloride, ammonia, peroxisomic compounds, silver and silver compound in solution, algae and other living agents.

In any of the above embodiments, stress may be applied to the growing or drying components to prompt further action from the fungus. For instance, stress pressure may be applied to a fungal molded shape that approximates the real world pressure that fungal shape is likely to receive when used as a part of a structure. Given enough pressure, cracks or fissures will form. Here, pressure may be released and the hyphae may be allowed to continue to grow, thereby not only filling in the cracks, but also causing new material to be formed, and hence increasing the strength, right in the region where it formerly was the weakest. As another example of method components that need not be taken in the order presented in exemplary embodiment FIG. 1, stress pressure may be applied to the lignocellulose based medium, prior to inoculation. Further, the stress pressure may be applied whether a mold is used or not. For instance, in the continuous feed embodiments, stress pressure, such the pulling apart of, twisting of, or compressing of the fungal mycelium may occur. Again, any weak points that form cracks or fissures will be grown over with new hyphae such that the fungal mycelium becomes stronger in the areas where it was formerly weaker.

All of the above discussed methods and embodiments offer the advantage of transforming agricultural or other waste into a durable industrial grade material that can serve a wide range of manufacturing and construction applications. The fungal material can be used to replace plastic or wood and may be combined with bamboo and other renewable materials to create hybrid composites. The fungal material is produced using considerably less energy than is required to create comparable hybrid composites. Additionally, the fungal material is biodegradable, durable and tunable. The building materials are fire resistant, water resistant, mold resistant and possess good insulative properties. The methods discussed herein make use of agricultural waste material, which may be effectively turned into high quality construction material at very low energy and production cost.

All of the above mentioned embodiments of the fungal material and variations thereon may be used for construction, packaging, and a wide variety of other uses. Such uses may include utility and application in environmentally sensitive areas for the purpose of creating any type of temporary or permanent artifact, particularly in projects focused on remediation or in areas particularly sensitive to industrial impact. The fungal material may be used where planned obsolescence for an object or limited use is desired, such as for consumer electronics casings and components in furniture. The fungal material may also be used to create biodegradable vessels, shelters, and intermediary forms used in land reclamation and conservancy. Once a structure that is composed from this material no longer serves a utility or purpose the structure might be broken down into smaller pieces on site and left to biodegrade. The fungus may also be grown into terraced forms such as the ones that are used in civil engineering and landscaping. The fungus may be employed to shape contoured earth forms, to create diversion streams, embankments, water elements, and retaining walls. It is known that mycelium have the ability to help clean nitrogen and other reactive compounds from soil and other organic substrates, and both strengthen soil composition and are a strong contributing factor towards the general health of the living ecologies that they are a part of. While serving a functional or structural purpose, materials used for these ends might also be used for novel applications in bioremediation. Mycelium of fungal species have evolved the ability to utilize super oxidative compounds and other strong lysosomic agents that are used to break lignocellulose into metabolizable sugars and other nutrients. The fungi are characterized by this transformational ability, and are the primary decomposers of the world's toughest organisms, organs, tissues, cells and component molecules. For these and other reasons the saprophytic fungi are capable of transforming, neutralizing and breaking down a wide range of biotoxic molecules and other noxious compounds. It has been recorded that some species of mushrooms have been grown on a lignocellulose compound saturated with used motor oil. The fungi are able to breakdown the complex molecular chains that are normally difficult to break down, such as macromolecules, biopolymers and certain organic compounds. For this reason it is believed that semi living structures can be incorporated as beneficial attributes and materials for bioremediation projects as well as for use in cleaning brown and grey field pollutants.

It is possible through careful and precise adjustments to create fungal blocks and fungal building materials that perform beyond those in the prior art, and may be prepared more simply and with less equipment than those in the prior art. Using methods described herein, fungal forms compressed around embedded forms exhibited adhesion strength at least four times stronger than a control.

The process is dependent on the frequency, duration and amount of pressure that is applied to the growing mycelium, and can be practiced in orchestration with several other variables to generate a wide variety of structural qualities such as toughness, flexibility, dynamic resistance, etc. In one instance, blocks and other construction materials may be formed in a way that placement in a mold and for solidification is not required.

Using the methods described herein, building blocks larger than those known in the prior art may be grown. Indeed, no apparent scale limitation was found in development. Furthermore, these forms may be made in a way that they do need to be placed in a mold for shaping and to solidify.

Using the methods described surrounding the multi-layering of pieces of laminated fungal mycelium, improved resistance to impact was found. In one instance, 8 layers of 1" thin pieces of grown fungus were glued together with paper board squares between each layer, such that the entire structure was 8.5" deep when glued together. In testing a hollow point bullet fired from a .38 came to rest within the last layer of fungus. FIG. 6. Depicts one such wall, which may be used for impact resistance. The wall exhibits sufficient strength to act as a load bearing wall within a building.

It is possible through careful and precise adjustments to create fungal blocks and fungal building materials that perform beyond those in the prior art, and may be prepared more simply and with less equipment than those in the prior art. Using methods described herein, fungal forms compressed around embedded forms exhibited adhesion strength at least four times stronger than a control. Further, these embedded forms can be processed and dried more quickly than other methods, and are achieved without greater substrate density or additional agents.

Further expected use of the methods described herein are in developing and rural settings, where the simplicity of tools and processes in the art in those areas will still allow for the generation of a wide range of durable, long lasting and resilient materials from lignocellulose waste sources. The fungal material finds potential uses in gardening and landscaping, civil engineering, including the regeneration of fungal mycelium through the timed germination and dispersal of companion plants and other life forms that may be embedded within a somatic form. The fungal structures can act as animal shelter, ground cover and general inert environmental scaffolding. Moreover, this fungal material may also be used to create strong lightweight shells and forms that may be used in the manufacture of boats, furniture, and other consumer or commercial products which currently employ cardboard honeycomb, fiberglass, plastics or other strong lightweight materials to create structured forms such as molded decorative tiles, molding, temporary advertising installations, and panel relief forms. The somatic substance may also be employed as a replacement for high impact thermoplastics, such as the casing shells for consumer electronics, components for industrial equipment and home appliance, and vehicle bumpers. Additionally, the somatic material has excellent compressive qualities and can absorb blunt forces, disperse seismic waves, and damp acoustic signals.

A molding system for forming an inoculated lignocellulose based medium into a fungal molded shape, the molding system comprising a vessel within which environmental conditions are regulated, the vessel comprising an inoculated lignocellulose based medium capable of supporting growth of saprophytic fungi without any secondary organisms displacing the process through infection; a secondary organic material layered near the top and bottom of the inoculated lignocellulose based medium; a hard mold containing the flexible vessel; and a compressive system for applying a primary compressive pressure of at least 10 PSI to the lignocellulose based medium such that it takes on a fungal molded shape.

A molding system comprising a first inoculated lignocellulose based medium; a second, grown inoculated lignocellulose based medium; a perforation layer between said first and second media; and whereby said second, grown inoculated lignocellulose based medium contains in it a cellulosic or non-cellulosic fabric.

The foregoing description of the preferred embodiment of the present invention has been presented for the purpose of illustration and description. It is not intended to be exhaustive or to limit the invention to the precise form disclosed. Many modifications and variations are possible in light of the above teachings. For instance, the inoculation or the pasteurization of the fungal substrate may occur after placement of the fungal substrate into the mold. Further, innovations in pasteurization, microbial suppression, or clean room design and control may be integrated into the manufacture process. Batch, continuous, or segmented production methods may also be employed to manufacture the fungal molded shapes. It is intended that the scope of the present invention not be limited by this detailed description, but by the claims and the equivalents to the claims appended hereto.

I claim:

1. A molding system for forming an inoculated lignocellulose based medium into a fungal molded shape, the molding system comprising:
   a. an inoculated lignocellulose based medium;
   b. a vessel within which environmental conditions are regulated, the vessel comprising the inoculated lignocellulose based medium that is saturated with water, the inoculated lignocellulose based medium further comprising nitrogen, trace elements, and a buffer to balance the pH of the inoculated lignocellulose based medium;
   c. the vessel capable of supporting growth of saprophytic fungi without any secondary organisms displacing the process through infection;
   d. a secondary organic material layered near the top and bottom of the inoculated lignocellulose based medium, the secondary organic material comprising a cross-grained laminate of at least two layers comprising components set at right angles relative to one another;
   e. a hard mold containing the flexible vessel; and
   f. a compressive system for applying a primary compressive pressure of at least 10 PSI to the lignocellulose based medium and a secondary compressive pressure of between 300-500 psi to the lignocellulose based medium such that at least some water is forced out of the medium, allowing it to absorb an agent and take on a fungal molded shape; wherein the compressive system further comprise an aqueous gel agent to be absorbed within the fungal mycelium to form the fungal molded shape; and
   g. a filter for filtering the inoculated lignocellulose based medium.

2. The molding system of claim 1 wherein said flexible vessel environmental conditions are between 55 and 90 degrees Fahrenheit.

3. The molding system of claim 1 wherein said flexible vessel environmental conditions include a hydration level of between 44% and 66%.

4. The molding system of claim 1 wherein said fungal molded shape comprises an outer surface of mycelium.

5. The molding system of claim 1 further comprising a plurality of fungal molded shapes in proximal contact with one another.

6. The molding system of claim 5 wherein said fungal molded shapes comprise an outer surface of mycelium; the inoculated lignocellulose based medium further comprising microcrystalline cellulose.

7. The molding system of claim 1 wherein said fungal molded shape has a weight of which at most 15% of said weight is made up of water.

8. The molding system of claim 1 wherein said fungal molded shape comprises fungal mycelium; the inoculated lignocellulose based medium further comprising microcrystalline cellulose.

9. The molding system of claim 8 wherein the fungal mycelium is in contact with secondary materials.

10. The molding system of claim 8 wherein said fungal molded shape has a weight of which at most 15% of said weight is made up of water.

11. The molding system of claim 1 wherein the compressive system is further for applying a secondary compressive pressure of at least 100 PSI.

12. The molding system of claim 1 wherein said primary compressive pressure is of at least 500 PSI.

13. A molding system comprising:
   a. a first inoculated lignocellulose based medium;
   b. the first inoculated lignocellulose based medium comprising nitrogen, trace elements, and a buffer to balance the pH of the first inoculated lignocellulose based medium;
   c. a second, grown inoculated lignocellulose based medium;
   d. a secondary material layered between said first and second media, the secondary material comprising a cross-grained laminate of at least two layers comprising components set at right angles relative to one another;
   e. a filter for filtering the inoculated lignocellulose based medium; and
   f. a compressive system for applying a primary compressive pressure of at least 10 PSI to the lignocellulose based medium and a secondary compressive pressure of between 300-500 psi to the lignocellulose based medium such that at least some water is forced out of the medium, allowing it to absorb an agent and take on a fungal molded shape; wherein the compressive system further comprise an aqueous gel agent to be absorbed within the fungal mycelium to form the fungal molded shape;
   g. whereby said second, grown inoculated lignocellulose based medium contains in it a cellulosic or non-cellulosic fabric.

14. The molding system of claim 13, wherein the first inoculated lignocellulose based medium is within a vessel in which environmental conditions are regulated.

15. The molding system of claim 14 wherein the vessel is within a hard mold; and wherein the first inoculated lignocellulose based medium further comprises microcrystalline cellulose.

16. The molding system of claim 13 wherein the grown inoculated lignocellulose based medium is capable of supporting growth of saprophytic fungi without any secondary organisms displacing the process through infection.

17. The molding system of claim 13 wherein the second inoculated lignocellulose based medium is dry and biologically inert.

18. The molding system of claim 13 wherein the second inoculated lignocellulose based medium is a compressed form of mycelium fungi.

19. The molding system of claim 13 wherein the second, grown inoculated lignocellulose based medium is selected from the group of fungal spawn consisting of: *Ganoderma lucidum, Ganoderma tsugae, Ganoderma oregonense, Fomes fomentarius, Trametes versicolor* and *Piptoporous betulinus*.

* * * * *